United States Patent [19]

Van Der Puy et al.

[11] Patent Number: 5,633,413

[45] Date of Patent: May 27, 1997

[54] CONTINUOUS PROCESS FOR THE PRODUCTION OF VINYLIDENE CHLORIDE TELOMERS

[75] Inventors: Michael Van Der Puy, Amherst; Timothy R. Demmin, Grand Island; David E. Bradley, Buffalo, all of N.Y.

[73] Assignee: AlliedSignal Inc., Morris County, N.J.

[21] Appl. No.: 512,575

[22] Filed: Aug. 8, 1995

[51] Int. Cl.$^6$ .......................... C07C 17/08; C07C 17/266; C07C 17/275

[52] U.S. Cl. .............................................................. 570/257

[58] Field of Search ............................................... 570/257

[56] References Cited

U.S. PATENT DOCUMENTS 5,395,997  3/1995  Van Der Puy .

FOREIGN PATENT DOCUMENTS 1146463  3/1969  United Kingdom .................. 570/257

Primary Examiner—Alan Siegel
Attorney, Agent, or Firm—Jay P. Friedenson

[57] ABSTRACT

A process for the continuous production of telomers $CCl_3(CH_2CCl_2)_nCl$ where n=1–3 (Formula I) by the continuous reaction of $CCl_4$ and vinylidene chloride in the presence of a solvent and a catalyst. The reaction to form $CCl_3(CH_2CCl_2)Cl$ proceeds at a reaction rate constant $k_1$. If n=1, $CCl_3(CH_2CCl_2)Cl$ is continuously removed from the reactor. If n=2, the removed $CCl_3(CH_2CCl_2)Cl$ reacts similarly with $CCl_4$ and $CH_2=CCl_2$ in a second reactor to form and remove $CCl_3(CH_2CCl_2)_2Cl$ under conditions to have a reaction rate constant $k_2$, wherein the ratio of the molar amounts of $CCl_4$ to $CCl_3(CH_2CCl_2)Cl$ reacted is greater than the ratio $k_2/k_1$. If n=3, the removed $CCl_3(CH_2CCl_2)_2Cl$ similarly reacts in a third reactor with $CCl_4$ and $CH_2=CCl_2$ to form $CCl_3(CH_2CCl_2)_3Cl$ under conditions to have a reaction rate constant $k_3$, wherein the ratio of the molar amounts of $CCl_4$ to $CCl_3(CH_2CCl_2)_2Cl$ reacted is greater than the ratio $k_3/k_2$.

14 Claims, 2 Drawing Sheets

1

CONTINUOUS PROCESS FOR THE PRODUCTION OF VINYLIDENE CHLORIDE TELOMERS

BACKGROUND OF THE INVENTION

1. Field of the Invention

The present invention pertains to the production of chlorocarbons, or more particularly to the continuous production of telomers of the type having the formula $CCl_3(CH_2CCl_2)_nCl$ where n=1-3 (Formula I) by the continuous reaction of $CCl_4$ and vinylidene chloride. Such compounds are useful intermediates for the production of hydrofluorocarbons such as $CF_3CH_2CF_2H$ and $CF_3CH_2CF_2CH_2CF_3$. The latter find use as non-ozone depleting blowing agents and non-ozone depleting cleaning solvents respectively.

2. Description of the Prior Art

The preparation of compounds of Formula I is not new. They have been prepared by the reaction of $CCl_4$ with vinylidene chloride using metallic salts or organic free radical initiators as a catalyst. However, all prior methods for the preparation of Formula I compounds require a batch reactor process. In this regard, U.S. Pat. No. 5,395,997, which is incorporated herein by reference, teaches the production of a mixture of telomers which must be separated by distillation.

Because vinylidene chloride is volatile and the addition of $CCl_4$ to vinylidene chloride is slow, such reactions are typically conducted under pressure and at temperatures of about 80°-150° C. Such a process is inefficient for the manufacture of large quantities since considerable time is spent cooling and removing the product mixture, recharging raw materials, and heating the reactants.

A problem in the art of preparing compounds of Formula I compounds is the control of the telomer distribution. While it is less difficult to limit n to 1, since $CCl_4$ is more reactive than the 3-carbon telomer, $CCl_3CH_2CCl_3$, it is much more difficult to stop at n=2 since the reactivity of the 3-carbon and 5-carbon telomers are approximately the same. The same is true of the 5-carbon vs. the 7-carbon telomers. Control of the reaction to give essentially only one telomer has not been readily achieved heretofore. It has been particularly difficult to achieve reaction control at suitable conversions of the reactants. Thus, when only the 5-carbon telomer has been desired, practical large scale preparations have been severely limited by low conversions due to relative reactivities and low reactor throughput due to the batch type process.

The present invention provides a means of increasing the efficiency of the manufacturing process for Formula I compounds, and provides a means for obtaining substantially only the 3-carbon, 5-carbon or 7-carbon telomer.

SUMMARY OF THE INVENTION

The invention provides a method for the continuous production of compounds having the formula $CCl_3(CH_2CCl_2)_nCl$ wherein n=1, 2 or 3. The method comprises continuously feeding into a reactor sufficient amounts of $CCl_4$ and $CH_2=CCl_2$, in the presence of a sufficient amount of at least one solvent and at least one catalyst to drive the reaction to form $CCl_3(CH_2CCl_2)Cl$ under conditions sufficient to have a reaction rate constant $k_1$. Then if n=1, one continuously removes $CCl_3(CH_2CCl_2)Cl$ from the reactor. If n=2, after continuous removal of $CCl_3(CH_2CCl_2)Cl$ from the reactor, one reacts the removed $CCl_3(CH_2CCl_2)Cl$ in a second reactor with sufficient amounts of $CCl_4$ and $CH_2=CCl_2$, in the presence of a sufficient amount of at least one solvent and at least one catalyst to drive the reaction to form $CCl_3(CH_2CCl_2)_2Cl$ under conditions sufficient to have a reaction rate constant $k_2$, wherein the ratio of the molar amounts of $CCl_4$ to $CCl_3(CH_2CCl_2)Cl$ reacted is greater than the ratio $k_2/k_1$, and then continuously removing $CCl_3(CH_2CCl_2)_2Cl$ from the second reactor. If n=3, after continuous removal of $CCl_3(CH_2CCl_2)_2Cl$ from the second reactor, one reacts the removed $CCl_3(CH_2CCl_2)_2Cl$ in a third reactor with sufficient amounts of $CCl_4$ and $CH_2=CCl_2$, in the presence of a sufficient amount of at least one solvent and at least one catalyst to drive the reaction to form $CCl_3(CH_2CCl_2)_3Cl$ under conditions sufficient to have a reaction rate constant $k_3$, wherein the ratio of the molar amounts of $CCl_4$ to $CCl_3(CH_2CCl_2)_2Cl$ reacted is greater than the ratio $k_3/k_2$ and then continuously removing $CCl_3(CH_2CCl_2)_3Cl$ from the third reactor.

DETAILED DESCRIPTION OF THE PREFERRED EMBODIMENT

Figure 1:
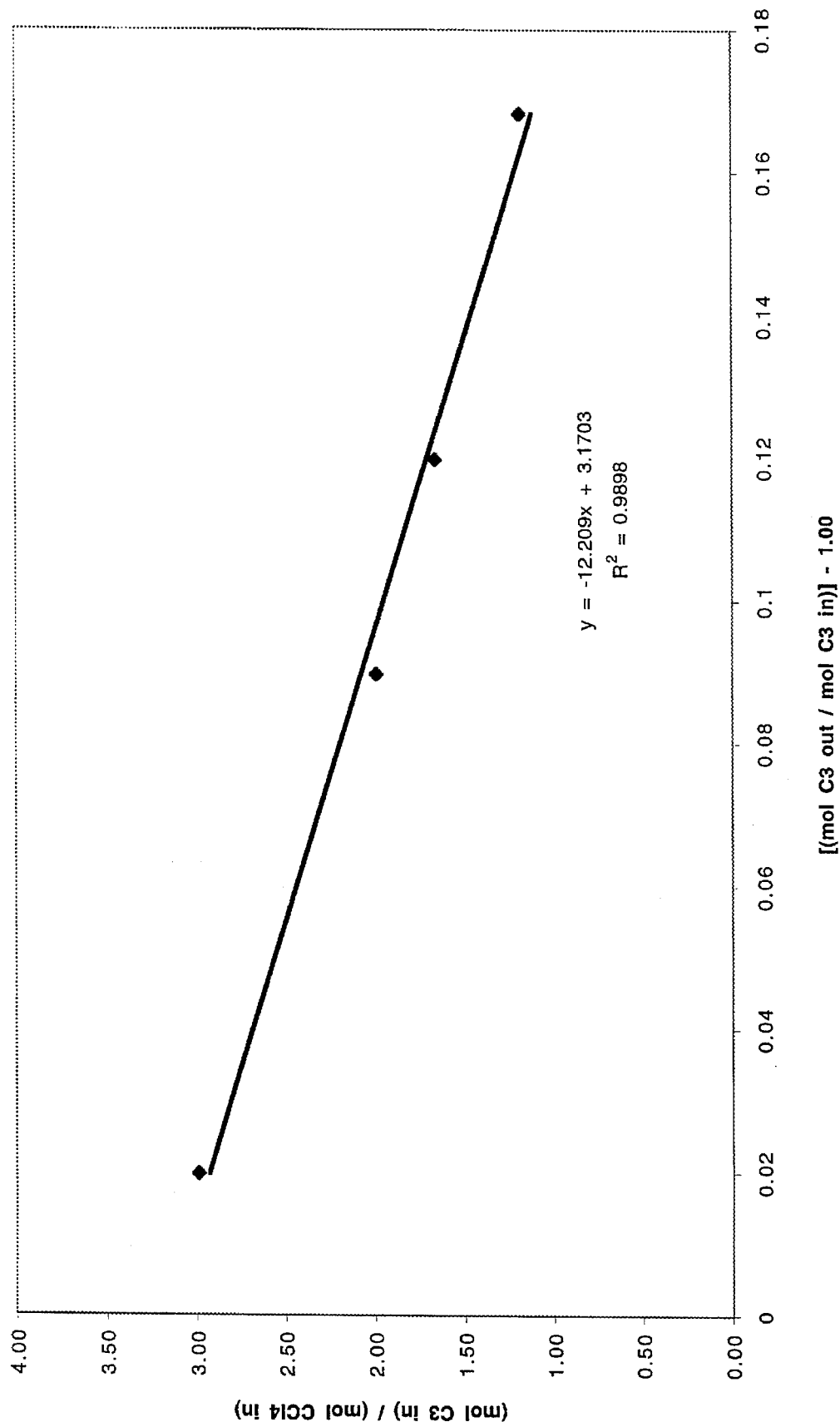
FIG. 1 shows a plot of Example 5 results which indicate that when the mole ratio of HCC-230 to $CCl_4$ is about 3.1:1, a steady state is achieved.

The telomers, $CCl_3CH_2CCl_3$ (referred to as HCC-230), $CCl_3CH_2CCl_2CH_2CCl_3$ (referred to as HCC-450), and $CCl_3(CH_2CCl_2)_3Cl$ (referred to as HCC-670) are prepared in a continuous fashion and with a minimum amount of higher molecular telomers using a continuous stirred tank reactor. For the preparation of essentially only HCC-230, $CCl_4$, vinylidene chloride, catalyst, and a solvent are continuously feed into the continuous stirred tank reactor maintained at a suitable reaction temperature, under pressure, while continuously removing some of the reactor product which, with proper control of the average residence time within the reactor, contains HCC-230 but little or no HCC-450 and higher telomers. The product stream leaving the continuous stirred tank reactor is fed into a flash distillation unit where unreacted $CCl_4$, vinylidene chloride, and solvent are evaporated, leaving only the product HCC-230 and insoluble catalyst, which is removed by filtration. The desired product is finally purified by distillation. The volatile materials and the recovered catalyst are preferably returned to the reactor, along with additional amount of reactants to maintain the desired reactant ratios within the continuous stirred tank reactor. The reaction conditions have been found to be exceedingly corrosive to many metals that are commonly employed as reaction vessels. Tantalum, teflon and glass lined steel reactors have been founds to be suitable.

Whether HCC-230, HCC-450 or HCC-670 is the desired product will effect the choice of reaction conditions, including temperature, residence times and reactant ratios for achieving the desired product. In order to achieve control of the telomerization reaction, it is important to choose conditions such that the reaction proceeds sequentially in consecutive reactions. This is achieved at relatively high catalyst concentrations and high saturated chlorocarbon to vinylidene chloride ratios. At the preferred concentrations of vinylidene chloride, the reactions are first order in CCl4. Since the concentration of the catalyst does not change, it can be incorporated into the rate constants (k) for the reactions. The rate equations for the three reaction steps can be represented by:

1. $CCl_4 + CH_2=CCl_2 \xrightarrow{k_1} CCl_3CH_2CCl_3$
2. $CCl_3CH_2CCl_3 + CH_2=CCl_2 \xrightarrow{k_2} CCl_3CH_2CCl_2CH_2CCl_3$
3. $CCl_3CH_2CCl_2CH_2CCl_3 + CH_2=CCl_2 \xrightarrow{k_3} CCl_3(CH_2CCl_2)_3Cl$ When only HCC-230 is desired, it is necessary to suppress the reaction of HCC-230 with vinylidene chloride, and when only HCC-450 is desired, it is necessary to suppress the next reaction of HCC-450 with vinylidene chloride. The rate constant k1 is larger than k2. The reaction of HCC-450 with vinylidene chloride is very nearly the same as k2 because of the structural similarity between HCC-230 and HCC-450. It is because only the terminal —CCl3 groups are reactive that control of the reaction to produce only one telomer is difficult.

For the first reaction step, the $CCl_4$ and vinylidene chloride are preferably reacted in a mol ratio of $CCl_4$ to vinylidene chloride ranging from about 10:1 to about 2:1. A more preferred range is from about 5:1 to about 3:1 and most preferably from about 3:5:1 to about 3:1. Each reaction step is conducted in the presence of a catalyst. Suitable catalysts non-exclusively include CuCl, $CuCl_2$ dihydrate, tungsten chloride, ferrous chloride and cuprous iodide. The most preferred catalyst has been found to be CuCl. The catalyst is preferably present in an amount of from about 3% to about 0.5% by weight of the composition, more preferably from about 2% to about 0.5% and most preferably from about 1.5% to about 1.0%. Suitable solvents include low molecular weight nitriles such as acetonitrile, propionitrile, and butyronitrile, which is present in an amount sufficient to form a uniform solution of the reactants. It has been found that nitrile solvents will co-ordinate with the catalysts in addition to dissolving the metal salt. In this regard the solvent and catalyst effectively form a catalyst-co-catalyst system for these reactions. The combination of CuCl with the nitrile solvent proves to be very selective, recyclable, inexpensive and gives adequate reaction rates.

The solvent is preferably present in the overall composition in the continuous stirred tank reactor in an amount of from about 50 wt % to about 10 wt %, more preferably from about 30 wt. % to about 15 wt. % and most preferably from about 25 wt. % to about 20 wt %.

In the preferred embodiment, each reaction step is conducted at a temperature of from about 100° C. to about 150° C., or more preferably from about 115° C. to about 145° C., and most preferably from about 130° C. to about 140° C. At temperatures lower than 100° C., the reaction rates are unacceptably slow, while at temperatures over 160° C. both thermal decomposition of the HCC-230 and HCC-450 compounds into olefins and HCl plus the formation of polymeric tarry residues result.

Due to the volatile nature of vinylidine chloride, as well as the vapor pressure contribution from the solvent, CCl4 and the azeotropes, high temperatures result in high pressures. This is a problem when coupled to the corrosive nature of the reaction system to most metals. A trade-off then must occur between the reactor pressure limitations and the reaction temperature determined pressure. This can be circumvented only by the use of high pressure glass lined or tantalum clad vessels. The reaction rates are, for a given composition, largely a function of temperature, and the higher the temperature the faster the reaction velocity.

As a result of the reactors required, the reaction has pressure limits of from about 50 to about 90 psig, more preferably from about 60 psig to about 80 psig, and most preferably from about 70 psig to about 75 psig. In the preferred embodiment, the each reaction step is conducted for a sufficient time to provide a residence time of from about 2 hours to about 12 hours, or more preferably from about 2 hours to about 6 hours, and most preferably from about 2 hours to about 3 hours.

Similarly, the second process step for preparing HCC-450 is analogous, i.e. under the same reaction conditions, except that the feed materials include HCC-230, in addition to $CCl_4$, vinylidene chloride, catalyst and solvent. In this case limiting the product to HCC-450 not only depends on the reaction temperature and average residence time, but also on the $CCl_4$ to HCC-230 ratio within the reactor. When only HCC-450 is desired, it is convenient to operate the system in such a way that HCC-230 is neither consumed or produced as a by-product. To accomplish this in practice, both HCC-230 and $CCl_4$ are employed as reactants, along with vinylidene chloride. The relative proportion of $CCl_4$ and HCC-230 is such that the amount of HCC-230 formed from $CCl_4$ (reaction 1) is equal to the amount of HCC-450 formed from HCC-230 (reaction 2). When HCC-450 is desired, i.e. when n=2 in Formula 1, the mol ratio of $CCl_3CH_2CCl_3$, $CCl_4$ and vinylidene chloride employed as reactants ranges from about 6:1:2 to about 2:1:2. A more preferred range is from about 4:1:2 to about 2.5:1:2 and most preferably from about 3.5:1:2 to about 3.0:1:2. When only HCC-450 is desired, it is particularly convenient to control the operation such that the amount of HCC-230 that is returned to the reactor is constant i.e., neither a surplus inventory of HCC-230 results, nor is an additional source of HCC-230 required. That is, the net rate of producing HCC-230 is zero.

$$\frac{d[CCl_3CH_2CCl_3]}{dt} = k_1[CCl_4] - k_2[CCl_3CH_2CCl_3] = 0 \qquad 3.$$

$$k_1[CCl_4] = k_2[CCl_3CH_2CCl_3] \qquad 4.$$

$$\frac{k_2}{k_1} = \frac{[CCl_4]}{[CCl_3CH_2CCl_3]} \qquad 5.$$

From Equations 3–5 it is seen that this condition will be met when the ratio of concentrations is the inverse of the rate constants (Equation 5), provided that the reactions are first order in catalyst and saturated chlorocarbon and that the reactions are consecutive. In the continuous stirred tank reactor, it is desirable that the total mass or volume in the reactor remain constant. Thus the rate at which reactants are fed into the reactor must equal the rate at which the product mixture is withdrawn. The average residence time within the reactor, tau, is given by $$\text{tau} = \frac{M}{\underline{M}} \qquad 6.$$

where M is the total mass within the reactor and $\underline{M}$ is the mass flow rate out of the reactor which is equal to the rate of adding mass to the reactor. The net HCC-450 production rate is then $\underline{M}$ times the weight fraction of HCC-450 in the product mixture being continuously removed from the reactor.

7. HCC-450 production rate=(weight fraction HCC-450)$\underline{M}$

Since the net change in concentration of $CCl_3CH_2CCl_3$ is zero, the rate at which HCC-450 increases will equal the rate at which the initial concentration of $CCl_4$ decreases, until the conversion of HCC-450 to $CCl_3(CH_2CCl_2)_3Cl$ becomes significant. Consequently, $$\text{lambda} = \frac{X_A}{k_1(1-X_A)} \qquad 8.$$

where $X_A$ is the fraction of the initial $CCl_4$ concentration which has been converted.

Thus, in order to operate the continuous stirred tank reactor such that HCC-450 is produced to the exclusion of HCC-670 (CCl3(CH2CCl2)3Cl), it is necessary to experimentally determine the reaction rate constants and the point ($X_A$) at which HCC-670 is at the maximum allowable concentration. A typical product distribution curve for a batch reaction is shown in Table 1, where the ratio of rate constants $k_1/k_2$ (3/1) is the inverse of the initial $CCl_4$/HCC-230 concentration ratio. Calculated concentrations of the various reactants and products are shown in Table 1.

TABLE 1

Calculated Concentrations vs. Time

| T(h) | [CCl$_4$] | [HCC-230] | [HCC450] | [HCC-670] |
|---|---|---|---|---|
| 0 | 0.7500 | 2.2500 | 0.0000 | 0.0000 |
| 1 | 0.7278 | 2.2497 | 0.0224 | 0.0001 |
| 2 | 0.7063 | 2.2486 | 0.0445 | 0.0004 |
| 3 | 0.6854 | 2.2471 | 0.0665 | 0.0010 |
| 4 | 0.6652 | 2.2449 | 0.0882 | 0.0017 |
| 5 | 0.6455 | 2.2421 | 0.1096 | 0.0027 |
| 6 | 0.6265 | 2.2388 | 0.1308 | 0.0040 |
| 7 | 0.6079 | 2.2349 | 0.1518 | 0.0053 |
| 8 | 0.5900 | 2.2305 | 0.1725 | 0.0070 |
| 9 | 0.5725 | 2.2257 | 0.1930 | 0.0088 |
| 10 | 0.5556 | 2.2204 | 0.2131 | 0.0108 |

After 8 hours of reaction time, 21% of the $CCl_4$ has been converted, the HCC-230 concentration is greater than 99% of its original concentration, and the ratio of HCC-450 to HCC-670 is 25 to 1. Similar data, using rate constants determined at any desired operating temperature, can be used to select an acceptable value for $X_A$. The determination of $X_A$ from the batch reactor gives an approximate value of the residence time in the continuous stirred tank reactor. The optimum value of lambda in the continuous reactor can be found by changing lambda incrementally and determining its effect on the amount of HCC-450 and HCC-670 produced.

The reactor operation is flexible, such that both HCC-230 and HCC-450 may be produced, if desired. In this case, the ratio of [$CCl_4$]/[HCC-230] in the reactor should be >k2/k1 so that more HCC-230 is produced than is added and its net production is therefore greater than zero. In the limiting case, when the concentration of $CCl_4$ is high and no HCC-230 is initially present, HCC-230 can be produced without significant amounts of HCC-450.

If HCC-450 is the desired product, the product from this reactor, after removing the volatiles and catalyst, consists of a mixture of HCC-230 and HCC-450, which are separated conveniently by distillation. The recovered HCC-230 is returned to the continuous stirred tank reactor.

The third process step for preparing the telomer $CCl_3(CH_2CCl_2)_3Cl$ which is known as HCC-670 is also done analogously, i.e. under the same conditions as above, except that the feed materials include HCC-230, HCC-450, vinylidene chloride, catalyst, solvent, and optionally $CCl_4$. When HCC-670 is desired, the mol ratio of HCC-450, HCC-230, $CCl_4$ and vinylidene chloride employed as reactants ranges from about 2:2:1:2 to about 1:1:0:1. A more preferred range is from about 1:2:0.2:1 to about 0:2:0:1 and most preferably from about 1:3:0.2:1 to about 0:3:0:1.

The following non-limiting examples serve to illustrate the invention.

EXAMPLE 1

An autoclave is charged with 1 g of a 1:1 by weight of a mixture of CuCl and CuCl$_2$ dihydrate as catalyst, 91.6 g (15 ml, 0.595 mol) $CCl_4$, 127 ml acetonitrile and 18.6 g (15 ml, 0.192 mol) vinylidene chloride, for a total volume of 200 ml.

The autoclave is evacuated briefly using a vacuum and heated to 130°-133° C. for 20 hours (maximum pressure about 115 psig). The mixture is poured into 200 ml water, and the lower layer separated. The aqueous layer is extracted 2×25 ml CH$_2$Cl$_2$, and combined with the original organic layer. The volume of the combined organic layers, after drying with Na$_2$SO$_4$ and filtering, is adjusted to 200 ml using CH$_2$Cl$_2$. A 5 ml aliquot is taken and CCl$_3$CH$_2$CH$_2$Cl (about 0.25 g) is added as an internal standard. Using established response factors, the quantities of products are determined: CCl$_3$CH$_2$CCl$_3$, 33.34 g (0.133 mol); CCl$_3$CH$_2$CCl$_2$CH$_2$CCl$_3$, 0.92 g (0.0026 mol). Since the ratio of HCC-230/HCC-450 is >50, it is concluded that under these conditions, the reactions are indeed consecutive and an estimate of the rate constant for the conversion of $CCl_4$ to HCC-230 is valid. The expression, kt=ln($CCl_{4\ t=0}$/$CCl_{4\ t=20}$) is used in which the moles of $CCl_4$ after 20 hours is determined as 0.595−0.133−0.0026=0.459, and for which the catalyst concentration is incorporated into k. Thus k=[ln (0.595/0.459)]/20=0.013 h$^{-1}$. This assumes that the reaction is first order in $CCl_4$ (and CuCl, which is incorporated into k). This assumption is consistent with the literature (J. Chem. Soc., Perkin II, 1973, 1000). In this reference, the rate was found to be independent of olefin concentration and the second order rate constant for $CCl_4$ additions catalyzed by CuCl at 110° C. was about 0.004 sec$^{-1}$. Dividing by the CuCl concentration of 0.005M, we obtain an average first order (catalyst concentration incorporated into k) rate constant of 0.84×10$^{-6}$ sec$^{-1}$ or 0.003 h$^{-1}$ at 110° C. Assuming a doubling of rate for each 10 degree rise in temperature, the literature value leads to an estimated k of 0.012 h$^{-1}$ at 130° C., which is in good agreement with the value obtained. It is important to realize that modelling efforts based on these rate constants require that conditions exist which assure a consecutive series of reactions. In addition to GC methods, the product distribution can be obtained by nmr. This is especially important if substantial HCC-670 is obtained since a pure GC standard is not available. The —CH$_2$— singlet for HCC-230 is distinct at delta=4.14, while the —CH2— for HCC-450 is at delta 4.04, which overlaps with the outer —CH$_2$— protons of HCC-670 (CCl$_3$(CH$_2$CCl$_2$)$_3$Cl). The inner —CH$_2$— of HCC-670, however, is a singlet at delta 3.85. Thus the contribution HCC-670 makes to the 4.04 peak is simply twice the integrated value of the 3.85 signal. Hence each telomer can be quantified by integration of the proton nmr signals. If higher telomers are formed, the analysis is more involved, and the product distribution is more conveniently represented by the degree of polymerization. This example establishes conditions which assures a sequential series of reactions, estimates a rate constant for HCC-230 formation, and prepares HCC-230 without HCC-450 formation.

EXAMPLE 2

A Teflon lined autoclave is charged with 150 ml CCl$_4$, 150 ml acetonitrile, 1.03 g of catalyst (same as prior Example), evacuated briefly, then charged with 58.6 g (0.604 mol) vinylidene chloride, and finally pressurized to 20 psig with nitrogen. The total volume is about 60% of the available autoclave volume. The mixture is stirred (350 rpm) and heated to 130°-133° C. for 16.5 hours. Volatiles are removed (rotary evaporation) leaving 145.5 g liquid and solid (catalyst). The liquid (144.5 g) is analyzed by GC and found to consist of 129.1 g (0.514 mol) of HCC-230, and 12.4 g (0.036 mol) of HCC-450; HCC-670 was not detected. The percent of vinylidene chloride accounted for by HCC-230 and HCC-450 is 97%. Hence the maximum amount of HCC-670 that could have been present is 0.006 mol. The 145.5 g obtained, including the solid, is returned to the autoclave, along with 75 ml fresh acetonitrile, and 20.3 g vinylidene chloride following the procedure described above. Heating to 131°–132° C. is resumed for 20 hours. At this time GC analysis indicates the presence of 110.7 g (0.441 mol) of HCC-230, 34.6 g (0.099 mol) of HCC-450, and approximately 3.35 g (0.0075 mol) of HCC-670, representing a HCC-230 conversion of 14.3% and a vinylidene chloride conversion of 36%. This example presents an alternate procedure for preparing HCC-230. Some HCC-450 is co-produced, but almost no HCC-670 is produced. The process is likely first order, and consecutive. Recycle of the crude product, together with catalyst, is also demonstrated.

EXAMPLE 3

In a manner similar to the prior Example, an autoclave is charged with 150 ml $CCl_4$, 150 ml acetonitrile, 1.02 g catalyst, 57.7 g (0.595 mol) vinylidene chloride, and 20 psig $N_2$. After heating to 148°–152° C. for 4 hours, the contents are cooled and analyzed without workup. The results indicate 128.1 g of HCC-230 (0.510 mol) and 13.7 g (0.039 mol) of HCC-450. After removing the volatiles, there remained 140.4 g crude material which is comprised of 86.3% of HCC-230, 11.4% of HCC-450, and 0.80% of HCC-670 by GC Analysis. Distillation at 2.7 mm Hg gives 114.3 g of 99.7% pure HCC-230, b.p. 63°–65° C. (77% yield). This example shows that substantially equivalent results can be obtained at 150° C. for 4 hours, where the maximum pressure is 160 psig, including the nitrogen that is added. In this Example, the vinylidene chloride conversion is at least 99%, while in a experiment at 150° C. for 2 hours, the conversion is 93%.

EXAMPLE 4

An autoclave is charged with 150.0 g $CCl_3CH_2CCl_3$, 75 ml acetonitrile, 31.0 g vinylidene chloride and 1 g of catalyst as in the prior Example, and 20 psig of $N_2$ as described above. The contents are stirred and heated to 131° C. for 24 hours. GC analysis is performed in duplicate and indicates the presence of 116.5 g of HCC-230, 47.8 g of HCC-450, and about 5.6 g of HCC-670 (total weight by GC=169.9 g). After removing the volatiles, there remained 168.3 g. The conversion of HCC-230 is 22.4%. This example shows the preparation of HCC-450 from HCC-230. By nmr analysis, the mole ratio of HCC-450 to HCC-670 is 9.6, which is in good agreement with the value estimated by GC analysis (8.6).

EXAMPLE 5

Figure 2:
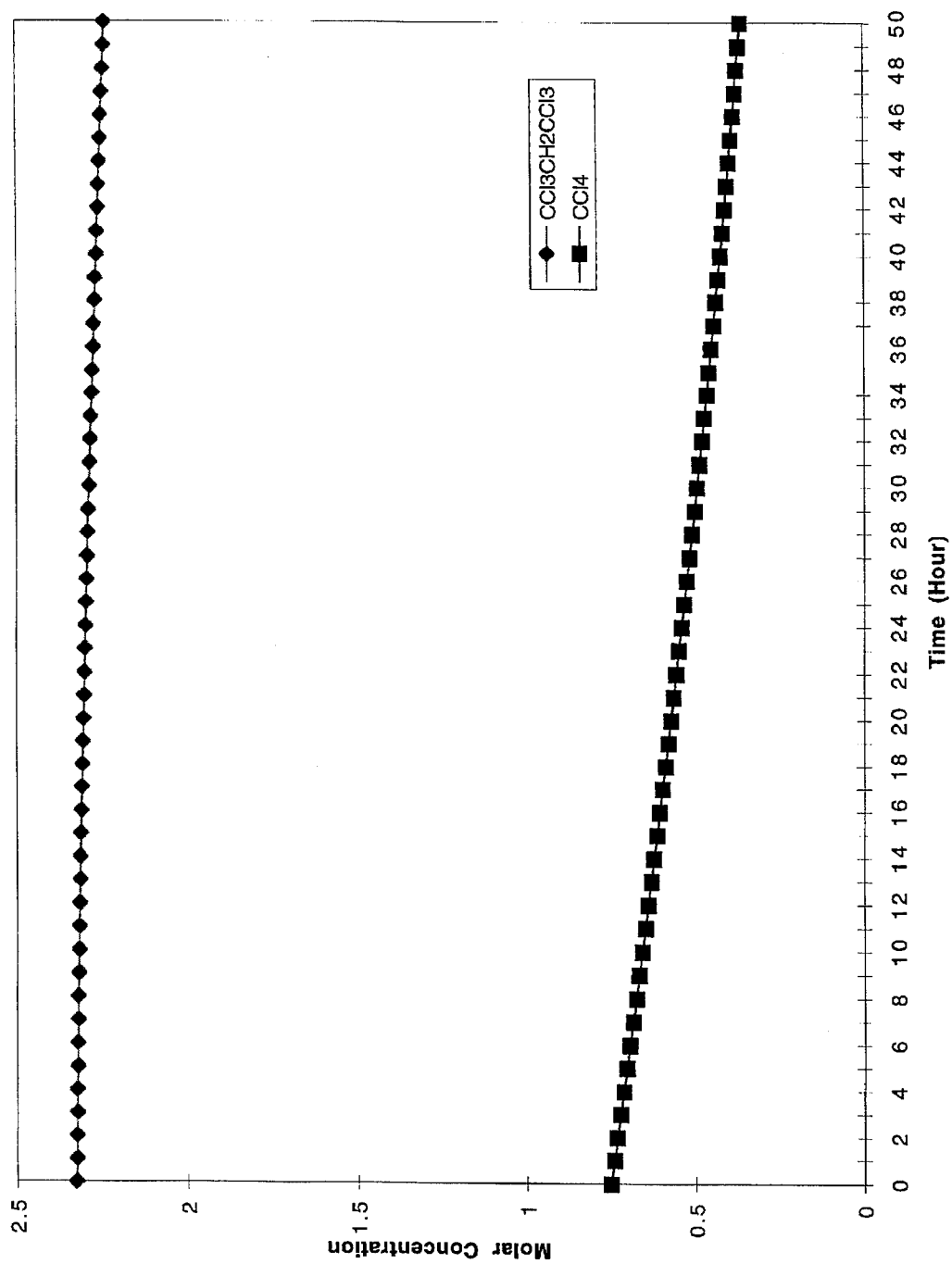
FIG. 2 shows a plot of Example 5 results which indicate $CCl_4$ and HCC-230 concentrations as a function of time.

Kinetic modelling requires that the relative reaction rates for HCC-230 formation from $CCl_4$ ($k_1$) and HCC-450 from HCC-230 ($k_2$) be known under first order, consecutive reaction conditions. Since these conditions are established in Example 1, the ratio of $k_1/k_2$ is determined by repeating Example 1, except the original $CCl_4$ volume is substituted for a mixture of $CCl_4$ and HCC-230. The total volume (200 ml), catalyst concentration (1 g), vinylidene chloride concentration (15 ml), reaction temperature (130° C.) and time (20 hours) are constant. Different ratios of HCC-230 to $CCl_4$ are used, and the ratio of HCC-230 to $CCl_4$ that goes into the reactor is plotted against the ratio of HCC-230 (out as product)/HCC-230(in as reactant) that is obtained after 20 hours. The results indicate that when the mole ratio of HCC-230 to $CCl_4$ is about 3.1:1, a steady state is achieved, i.e. the amount of HCC-230 at the end is the same as the amount added. This is shown in FIG. 1. An approximate $k_2$ value is therefore 0.004 $h^{-1}$. A plot of $CCl_4$ and HCC-230 concentrations as a function of time using these rate constants and initial concentrations of 0.75M for $CCl_4$ and 2.325M (116.6 g in 200 ml) for HCC-230 is shown in FIG. 2. After 20 hours, the concentration of HCC-230 is still >99% of its initial value. The following rate expressions are used: $CCl_4=A=A_0 e^{k_1 t}$ and $HCC\text{-}230=B=(A_0 k_1/k_2-k_1)(e^{-k_1 t}-e^{-k_2 t})+B_0 e^{-k_2 t}$. The maximum concentration of $C_5$ and higher telomers must be equal to the decrease in $CCl_4$ concentration. After 20 hours, this is 0.172M or 12.1 g of $C_5$ in a 200 ml batch size assuming no HCC-670 and higher telomers. No HCC-670 is observed in a 20 hour run at 131° C. when the initial ratio of HCC-230/$CCl_4$ is 2.95; the estimated (nmr) amount of HCC-450 is 15.4 g.

EXAMPLE 6

Calculation of the Residence Time, t

It is determined, by independent measurement, that under the desired operating conditions of temperature and catalyst concentration, $k_1$ is 0.040 $h^{-1}$. The reactions are zero order in vinylidene chloride concentration. Further, it is determined by analyzing the telomer distribution as a function $CCl_4$ conversion in a batch experiment (Table 1), that a $CCl_4$ conversion of 20% is possible without exceeding a HCC-670 limit which is arbitrarily set at <5% relative to HCC-450. The residence time in the reactor, is then calculated from Equation 8 as (0.2)/(0.04)(0.8)=6.25 hours.

EXAMPLE 7

Calculation of HCC-450 Production Rate

The density of the reaction mixture used to determine the data in Table 1 is measured to be 1.18 Kg/L using acetonitrile as the solvent. A total of 142.4 gallons of this reaction mixture (1400 lb) is charged to a 250 gallon continuous stirred tank reactor, and the contents are heated to 130° C. The rate of mass flow exiting the reactor is calculated from Equation 6 as 1400 lb/6.25 h or 224 lb/h. In the effluent mixture the weight percent HCC-450 is calculated as (100)(0.75)(0.2)(348)/1180=4.4. Hence the HCC-450 production rate, calculated from Equation 7, is (224)(0.044)=9.86 lb/h or 236.5 lb/day.

EXAMPLE 8

Calculation of Feed Rates

In order to maintain a constant mass and volume within the continuous stirred tank reactor, the amount of HCC-230, catalyst and solvent to be added as continuous input reactants must equal the amount removed as continuous output products. The amount of $CCl_4$ to be added is equal to the amount of unreacted $CCl_4$ removed plus 0.44 lb for each lb of HCC-450 removed (one molar equivalent). The amount of vinylidene chloride that must be added is the amount of unreacted vinylidene chloride removed plus 0.56 lb for each pound of HCC-450 removed (2 moles vinylidene chloride per mole of HCC-450). This example shows that HCC-450 can be made by a continuous process, overcoming the inherent inefficiencies of a corresponding batch process, while avoiding significant co-production of undesirable HCC-670. A key element in the continuous process is co-feeding HCC-230 and carbon tetrachloride in a ratio such that the change in HCC-230 concentration is zero.

What is claimed is:

1. A method for the continuous production of compounds having the formula:

$$CCl_3(CH_2CCl_2)_nCl$$

wherein n=2 or 3, which comprises
   (a) continuously feeding into a reactor sufficient amounts of $CCl_4$ and $CH_2=CCl_2$, in the presence of a sufficient amount of at least one solvent and at least one catalyst to drive the reaction to form $CCl_3(CH_2CCl_2)Cl$ wherein the reaction rate constant is $k_1$; and
   (b) if n=2, after continuous removal of $CCl_3(CH_2CCl_2)Cl$ from the reactor, reacting the removed $CCl_3(CH_2CCl_2)Cl$ in a second reactor with sufficient amounts of $CCl_4$ and $CH_2=CCl_2$, in the presence of a sufficient amount of at least one solvent and at least one catalyst to drive the reaction to form $CCl_3(CH_2CCl_2)_2Cl$ wherein the reaction rate constant is $k_2$, wherein the ratio of the molar amounts of $CCl_4$ to $CCl_3(CH_2CCl_2)Cl$ reacted is greater than the ratio $k_2/k_1$; and then continuously removing $CCl_3(CH_2CCl_2)_2Cl$ from the second reactor; and
   (c) if n=3, after continuous removal of $CCl_3(CH_2CCl_2)_2Cl$ from the second reactor, reacting the removed $CCl_3(CH_2CCl_2)_2Cl$ in a third reactor with sufficient amounts of $CCl_4$ and $CH_2=CCl_2$, in the presence of a sufficient amount of at least one solvent and at least one catalyst to drive the reaction to form $CCl_3(CH_2CCl_2)_3Cl$ wherein the reaction rate constant is $k_3$, wherein the ratio of the molar amounts of $CCl_4$ to $CCl_3(CH_2CCl_2)_2Cl$ reacted is greater than the ratio $k_3/k_2$ and then continuously removing $CCl_3(CH_2CCl_2)_3Cl$ from the third reactor.

2. The method of claim 1 wherein the reactions are each conducted in the presence of a catalyst selected from the group consisting of CuCl, $CuCl_2$ dihydrate, tungsten chloride, ferrous chloride and cuprous iodide.

3. The method of claim 1 wherein catalyst is present in each reaction step in an amount of from about 0.5 wt % to about 3.0 wt % by weight of the composition.

4. The method of claim 1 wherein the reactions are each conducted in the presence of a solvent selected from the group consisting of acetonitrile, propionitrile and butyronitrile.

5. The method of claim 1 wherein each reaction is conducted in a continuous stirred tank reactor which is lined with a material selected from the group consisting of tantalum, teflon and glass lined steel.

6. The method of claim 1 wherein step (a) is conducted at a mol ratio of $CCl_4$ to vinylidene chloride ranging from about 10:1 to about 2:1.

7. The method of claim 1 wherein each reaction step is conducted at a temperature of from about 100° C. to about 150° C.

8. The method of claim 1 wherein each reaction step is conducted at a pressure of from about 50 to about 90 psig.

9. The method of claim 1 wherein each reaction step is conducted at a residence time of from about 2 hours to about 12 hours.

10. The method of claim 1 wherein n=2 and no substantial amount of $CCl_3(CH_2CCl_2)_nCl$ is produced where n=1 or 3.

11. The method of claim 1 wherein n=2 and the mol ratio of $CCl_3CH_2CCl_3$, $CCl_4$ and vinylidene chloride employed as reactants ranges from about 6:1:2 to about 2:1:2.

12. The method of claim 1 wherein n=3 and no substantial amount of $CCl_3(CH_2CCl_2)_nCl$ is produced where n=1 or 2.

13. The method of claim 1 wherein n=3 and the mol ratio of $CCl_3(CH_2CCl_2)_2Cl$, $CCl_3(CH_2CCl_2)Cl$, $CCl_4$ and vinylidene chloride employed as reactants ranges from about 2:2:1:2 to about 0:3:0:1.

14. The method of claim 1 wherein the rate at which reactants are fed into the reactor for each step approximately equals the rate at which product $CCl_3(CH_2CCl_2)_nCl$ is withdrawn.

* * * * *